(12) United States Patent
Laramee et al.

(10) Patent No.: US 7,112,785 B2
(45) Date of Patent: Sep. 26, 2006

(54) METHOD FOR ATMOSPHERIC PRESSURE ANALYTE IONIZATION

(75) Inventors: James A. Laramee, Edgewood, MD (US); Robert B. Cody, Portsmouth, NH (US)

(73) Assignee: JEOL USA, Inc., Peabody, MA (US)

( * ) Notice: Subject to any disclaimer, the term of this patent is extended or adjusted under 35 U.S.C. 154(b) by 109 days.

(21) Appl. No.: 11/034,450

(22) Filed: Jan. 12, 2005

(65) Prior Publication Data

US 2005/0196871 A1   Sep. 8, 2005

Related U.S. Application Data

(63) Continuation-in-part of application No. 10/732,205, filed on Dec. 10, 2003, now Pat. No. 6,949,741.

(60) Provisional application No. 60/460,179, filed on Apr. 4, 2003.

(51) Int. Cl.
   *H01J 49/10* (2006.01)
(52) U.S. Cl. .................. 250/288; 250/423 R; 250/424
(58) Field of Classification Search .................... None
   See application file for complete search history.

(56) References Cited

U.S. PATENT DOCUMENTS

| | | | |
|---|---|---|---|
| 4,546,253 A | 10/1985 | Tsuchiya et al. | |
| 5,192,865 A * | 3/1993 | Zhu | 250/288 |
| 5,684,300 A | 11/1997 | Taylor et al. | |
| 6,124,675 A | 9/2000 | Bertrand et al. | |
| 6,225,623 B1 | 5/2001 | Turner et al. | |
| 6,949,741 B1 * | 9/2005 | Cody et al. | 250/288 |
| 2002/0185593 A1 | 12/2002 | Doring | |

OTHER PUBLICATIONS

Mcluckey et al., "Atmospheric Sampling Glow Discharge Ionization Source for the Determination of Trace Organic Compounds in Ambient Air", *Anal. Chem.*, 60, 1988, pp. 2220-2227.

Kjichiro Otsuka et al., "An Interface for Liquid Chromatograph/Liquid Ionization Mass Spectrometer", *Analytical Sciences*, vol. 4, Oct. 1988, pp. 467-472.

Daniel R. Kojiro et al., "Determination of $C_1$-$C_4$ Alkanes by Ion Mobility Spectrometry", *Anal. Chem.*, 63, 1991, pp. 2295-2300.

Jianguo Zhao et al., "Liquid Sample Injection Using an Atmospheric Pressure Direct Current Glow Discharge Ionization Source", *Analytical Chemistry*, vol. 64, No. 13, Jul. 1, 1992, pp. 1426-1433.

John P. Guzowski, Jr. et al., "Development of a Direct Current Gas Sampling Glow Discharge Ionization Source for the Time-of-Flight Mass Spectrometer", *J. Anal. At. Spectrom.*, 14, 1999, pp. 1121-1127.

N. Leymarie et al., "Negative Ion Generation Using a MAB Source", presented at the Annual Meeting of the American Society of Mass Spectrometry, 2000 (2 pages).

C.A. Hill et al., "A Pulsed Corona Discharge Switchable High Resolution Ion Mobility Spectrometer-Mass Spectrometer", *Analyst*, No. 128, 2003, pp. 55-60.

Kenzo Hiraoka et al., "Atmospheric-Pressure Penning Ionization Mass Spectrometry", *Rapid Commun. Mass Spectrom.*, 18, 2004, pp. 2323-2330.

* cited by examiner

*Primary Examiner*—Jack I. Berman
(74) *Attorney, Agent, or Firm*—The Webb Law Firm (57) ABSTRACT

A nonradioactive atmospheric pressure method for ionization of analytes comprises creating an electrical discharge in a carrier gas thus creating metastable neutral excited-state species. The carrier gas containing the excited-state species is directed into a reactant gas to form ions of the reactant gas. The ionized reactant gas is then directed at the analytes at atmospheric pressure near ground potential to form analyte ions.

16 Claims, 8 Drawing Sheets

FIG.10A — GENUINE — ARTESUNATE $C_{19}H_{27}O_8^-$

FIG.10B — COUNTERFEIT

METHOD FOR ATMOSPHERIC PRESSURE ANALYTE IONIZATION

BACKGROUND OF THE INVENTION

1. Field of the Invention

The present invention relates to atmospheric ionization of analytes and mass spectrographic methods.

2. Description of Related Art

Regulatory and safety issues related to the use of radioactive materials, such as $^{63}$Ni, $^{241}$Am, and $^{3}$H, among others, have led to a search for non-radioactive ion sources for analytical instruments, such as ion mobility spectrometers. (See Turner et al. U.S. Pat. No. 6,225,623 entitled "Corona Discharge Ion Source for Analytical Instruments", Doring U.S. Patent Application Publication No. 2002/0185593 entitled "Ion Mobility Spectrometer with Non-Radioactive Ion Source".), and Kojiro et al., "Determination of $C_1$–$C_4$ Alkanes by Ion Mobility Spectrometry", *Anal. Chem.*, 1991, 63, 2295–2300.

Certain available corona discharge ion sources for atmospheric pressure ionization (API) mass spectrometers or ion mobility spectrometers (IMS) or chemical agent monitors (CAM) introduce the analyte (including solvent, air, and other contaminants) into the region containing a discharge needle. This leads to several problems:

1. The presence of oxygen or other contaminants in the air leads to degradation of the electrodes.

2. It can be difficult to maintain the discharge in the presence of contaminants, requiring a high electrical potential or pulsed potentials.

3. A corona discharge in air leads to the formation of species, such as $NO_2^-$, $NO_3^-$, and related cluster ions. These ions can cause a loss of sensitivity for analyte ions (C. A. Hill and C. L. P. Thomas, *Analyst*, 2003, 128, pp. 55–60) and can interfere with the detection of $NO_2^-$ and $NO_3^-$ produced from analytes containing nitro functional groups, such as nitro explosives or in the case of chloride ion interference with chlorate propellants for rocket motors or phosphate interference with chemical warfare-related compounds. Attachment of these mixed nitric oxides to explosive molecules will misrepresent the degree of nitration of the explosive. This is a serious drawback because the scale of explosive power is related to the degree of nitration on the molecule.

4. Introducing air and analyte into the discharge region limits the possibilities for controlling the nature of the chemical background to control the ion-formation chemistry.

Taylor et al. U.S. Pat. No. 5,684,300 entitled "Corona Discharge Ionization Source" and Turner et al. U.S. Pat. No. 6,225,623 B1 entitled "Corona Discharge Ion Source for Analytical Instruments" describe corona discharge ion sources, but do not describe separating the region where the discharge occurs from the region where the analyte is introduced. See also Zhao et al. entitled "Liquid Sample Injection Using Atmospheric Pressure Direct Current Glow Discharge Ionization Source," *Anal. Chem.*, 64, pp. 1426–1433, 1992.

Tsuchiya et al. U.S. Pat. No. 4,546,253 entitled "Apparatus for Producing Sample Ions" describes a method for using metastable atoms to produce ions from a sample introduced at the tip of an emitter needle downstream from the corona discharge. This technique requires that the sample be placed on or near an intense electric field emitter needle. See also Otsuka et al. entitled "An Interface for Liquid Chromatograph/Liquid Ionization Mass Spectrometer," *Analytical Sciences,* Vol. 4, October 1988. Tsuchiya has developed a technique called "Liquid Surface Penning Ionization" (LPI) that uses excited-state argon atoms produced in a corona discharge to ionize liquid samples. The liquid samples are deposited onto the tip of a heated needle at atmospheric pressure to which kilovolt electrical potentials are applied.

The present invention avoids use of an emitter needle at high electrical potential placed downstream of the corona discharge source. Further, the present invention provides a method of sampling neutral analyte molecules without the restriction of relocating the analyte from the surfaces on which they are attached. For example, cocaine from cash currency, and chemical/biological warfare agents from surfaces of military interest can be sampled directly and in situ without swabbing or solvent washing the surface. Each time sample is relocated, analyte molecules are lost (30 to 100% for trace-level concentrations). Therefore, direct surface sampling is always preferred.

Long-lived excited-state atoms and molecules (metastables) have been used in only a few other ion source designs. Bertrand et al. U.S. Pat. No. 6,124,675 entitled "Metastable Atom Bombardment Source" discloses a metastable atom source operating at reduced pressure for generating ions in a mass spectrometer. The device described requires substantially reduced pressures and does not describe means for using metastable atoms for atmospheric pressure ionization mass spectrometry or ion mobility spectrometers. The MAB source produces a beam of metastable atoms at reduced pressure that are introduced under vacuum into a conventional chemical ionization source. Analyte ions are produced by Penning ionization, a reaction between an energetic atom or molecule M* and a sample molecule S:

$$M^* + S \rightarrow S^+ + M + e^- \qquad (1)$$

A high degree of selectivity can be achieved by selecting species with excited-state energies just above the ionization potential of a specific analyte. Background interference with ionization potentials greater than the energy of the excited-state will not be ionized. The MAB source was tested in our laboratory and was found to be efficient and selective. However, it is limited to volatile analytes that can be introduced into a mass spectrometer vacuum system.

McLuckey and coworkers developed a technique called "Atmospheric Sampling Glow Discharge Ionization" (ASGDI) in which sample vapors are introduced through an orifice into a glow discharge at reduced pressure. McLuckey, S. A.; Glish, G. L.; Asano, K. G.; Grant, B. C., *Anal. Chem.,* 1988, 60, 2220. "Atmospheric Sampling Glow Discharge Ionization Source for the Analysis of Trace Organics in Ambient Air." Guzowski et al., *J. Anal. At. Spectrom.,* 1999, 14, 1121–1127 "Development of a Direct Current Gas Sampling Glow Discharge Ionization Source for Time-of-Flight Mass Spectrometer".

Hiraoka and coworkers recently reported atmospheric pressure Penning ionization mass spectrometry (APPeI) in which a gas stream was passed through an atmospheric pressure argon corona discharge to induce ionization prior to introduction into the atmospheric pressure interface of a time-of-flight mass spectrometer. Hiraoka, K.; Fujimaki, S.; Kambara, S.; Furuya, H.; Okazaki, S., *Rapid Commun. Mass Spectrom.,* 2004, 18, 2323–2330. "Atmospheric-Pressure Penning Ionization Mass Spectrometry".

All of these methods suffer from certain limitations that prevent direct analysis under ambient conditions. For example, MAB and ASGDI require that a volatile sample be introduced into a region of reduced pressure. LPI requires that the sample be placed on a heated needle that is held at high (kilovolt) electrical potentials. APPeI makes use of a ring of ten corona needles operated at kilovolt potentials surrounding the orifice into the mass spectrometer API interface. These factors hinder the ability to analyze samples directly without modification and without risk to the operator.

Furthermore, MAB, ASGDI, and APPeI introduce the sample directly into the electrical discharge region. It is well known that an electrical discharge can cause sample decomposition and unwanted reactions. In fact, corona discharge methods are used for the destruction of naval and cruse derived wastes.

SUMMARY OF THE INVENTION

Briefly, according to the present invention, there is provided a method of producing analyte, analyte fragment, and/or analyte adduct ions for mass spectrographic analysis. The method comprises the steps of introducing a carrier gas at atmospheric pressure into a chamber and establishing a potential difference in the chamber creating metastable neutral excited-state species. The carrier gas and metastable species are directed from the chamber into a reactant gas at atmospheric pressure, wherein the metastable species interact with the reactant gas to produce ionized derivatives of the reactant gas. The carrier-gas/reactant-gas/ionized-derivative mixture is directed into contact with the analyte maintained at atmospheric pressure and near ground potential to form analyte ions, analyte fragment ions, and/or analyte adduct ions. Preferably, the carrier gas consists substantially entirely of one or more of nitrogen and noble gases with an available metastable state high enough to cause ionization of the reactant gas. Preferably, the chamber comprises an electrode and a counter-electrode having a potential therebetween sufficient to cause an electrical discharge in the carrier gas.

According to one embodiment, the chamber comprises an electrode and a counter-electrode across which a high frequency signal is applied to cause an electrical discharge in the carrier gas.

According to another embodiment, the chamber comprises an electrode and counter-electrode each separated from the carrier gas by a dielectric barrier and having a potential therebetween sufficient to cause an electrical discharge in the carrier gas.

Preferably, the reactant gas is introduced into a second atmospheric pressure chamber and the ionized derivatives of the reactant gas are formed therein.

According to a preferred embodiment, the reactant gas comprises water vapor and the ionized derivatives being positive ion (protenated) water molecules and water molecule clusters.

According to another preferred embodiment, the reactant gas comprises oxygen and the ionized derivatives comprise negative oxygen ions and/or negative ion oxygen/water clusters.

According to yet another preferred embodiment, the reactant gas comprises ammonia and the ionized derivatives comprise positive ion ammonia and ammonia water ion clusters.

According to yet still another preferred embodiment, the reactant gas comprises a volatile organic halogen-containing molecule, such as trifluoroacetate.

It is an advantage, according to the present invention, that the analyte may be nonvolatile and that the analyte may be ionized at a liquid or solid surface.

According to a preferred embodiment of the present invention, there is provided a method for atmospheric pressure ionization comprising: into a first atmospheric pressure chamber introducing a carrier gas between a first electrode and a counter-electrode for creating a corona or glow electric discharge in the carrier gas causing the formation of neutral excited-state metastable species; directing the carrier gas from the chamber into a reactant gas maintained at atmospheric pressure to form intermediate ionized species in a mixture of the carrier gas and reactant gas and directing the mixture of carrier gas and reactant gas into contact with an analyte maintained at atmospheric pressure and near ground potential to form analyte ions, analyte fragment ions, and/or analyte adduct ions.

This method can be used to form positive or negative ions for use with spectrometers or other instruments which operate in the positive or negative ion mode. Typically, negative and positive ions are both formed when the analyte is brought into contact with the carrier-gas/reactant-gas/ionized-derivative mixture. Some analytes are electrophilic and tend to capture electrons to produce negatively charged analyte ions that allow detection and identification of these analytes. Others have a greater affinity for protons or positive ions and become ionized by picking up a proton $[M+H]^+$. This will guide the selection of a positive or negative ion mode.

In an apparatus for practicing the methods disclosed herein, a first electrode and counter-electrode must be maintained at potentials sufficient to induce an electrical discharge. The counter-electrode also serves to filter ionized species formed in the discharge. The potential difference between the first electrode and counter-electrode necessary for the formation of a discharge depends on the carrier gas and the shape of the first electrode, and is usually several hundreds of volts, say 400 to 1,200. But for small electron structures, such as those used in flat-screen plasma TV's, a few volts is sufficient. The first electrode, for example, a needle electrode, may have either a positive or negative potential. The counter-electrode is normally grounded or of polarity opposite to the needle electrode. This is the case whether operating in the positive ion or negative ion mode. In the positive ion mode, a lens electrode may be between ground potential and a few hundred positive volts to filter out negative ions in the carrier gas. Also, in the negative ion mode, a lens electrode may be between ground and minus a few hundred volts to filter out positive ions in the carrier gas.

By atmospheric pressure in this specification and the appended claims is meant pressures near ambient pressures, say 400 to 1,400 Torr. This would include pressurized aircraft and submerged submarines. For laboratory use, ambient pressures may fall within the range 700 to 800 Torr.

The carrier gas may be heated prior to introduction into the discharge or thereafter to facilitate vaporization or desorption of the analyte into the gas phase from surfaces.

BRIEF DESCRIPTION OF THE DRAWINGS

Further features and other objects and advantages will become clear from the following detailed description made with reference to the drawings in which.

DESCRIPTION OF THE PREFERRED EMBODIMENTS

Figure 1:
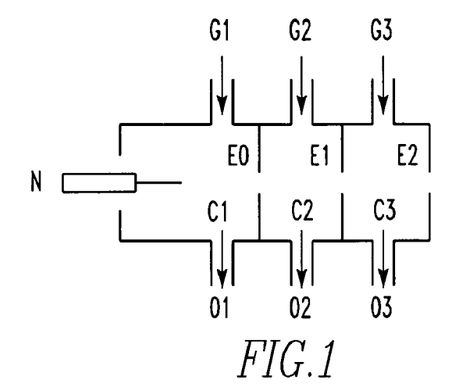
FIG. 1 is a schematic diagram of an atmospheric pressure ion source comprising aligned chambers C1, C2, and C3 useful according to the present invention.

Referring to FIG. 1 to an apparatus useful for practice of this method invention consists of a tube divided into several chambers through which a gas, such as nitrogen or helium, is allowed to flow. The gas is introduced into a discharge chamber where an electrical potential is applied between a discharge needle at kilovolt potentials and a perforated counter-electrode held at ground potential. A plasma consisting of ions, electrons, and excited-state species is produced in the discharge region. The gas is allowed to flow into an optional second chamber where a second perforated electrode can be biased to remove ions from the gas stream. The gas flow passes through a third region that can be optionally heated. Gas exits through a third perforated electrode or grid and is directed toward the mass spectrometer sampling orifice. The grid serves two functions: it acts as an ion repeller and it serves to remove ionic species of the opposite polarity thereby preventing signal loss by ion-ion recombination. The gas flow can be directed toward a liquid or solid sample, or it can interact with vapor-phase samples.

A typical reaction sequence is shown below using helium to form the initial excited-state molecules.

1. Formation of excited-state atoms of molecules ($e^-$=electron):

$$He^0(\text{electrical discharge}) \rightarrow He^+ + e^-$$

$$He^+ + e^- \rightarrow He^*$$

The $He^{*3}S1$ state has an energy of 19.8 eV which is above the ionization potential of water 912.6 eV.

2. Formation of charged water clusters:

$$He^* + H_2O \rightarrow H_2O^+ + He + e^-$$

$$H_2O^+ + H_2O \rightarrow H_3O^+ + OH$$

$$H_3O^+ + (H_2O)_n \rightarrow [(H_2O)_nH]^+$$

3. Reaction of charged water clusters to ionize target analyte molecule M:

$$[(H_2O)_nH]^+ + M \rightarrow [M+H]^+ + (H_2O)_n$$

Other reactions are possible. Atmospheric ions, such as oxygen, carbon dioxide and nitrogen, are not ionized by the water cluster ions. This provides additional selectivity for detecting trace levels of poisons, pollutants, etc., when air is present.

In the negative-ion mode, oxygen atoms can be ionized by reactions such as:

$$He^* + O_2 \rightarrow O_2^+ + He + e^-$$

The electron loses kinetic energy by collisions with gas molecules.

$$O_2 + e^- \rightarrow O_2^-$$

$$O_2^- + H_2O \rightarrow [H_2O\ O_2]^-$$

If helium is used as the carrier gas, the principal excited-state species has an energy of 19.8 eV. This energy is sufficient to ionize most molecules. Under normal conditions, the excited-state helium rapidly reacts with atmospheric moisture to produce positive-ion water clusters or negative-ion clusters containing oxygen and water. The reaction between excited-state helium and water molecules is extremely rapid.

A generalized apparatus useful for practice of the present invention is shown schematically in FIG. 1. This device provides an electrode N, for example, a needle electrode, to which an electrical potential can be applied in a first atmospheric pressure chamber C1 into which a carrier gas can be introduced through gas inlet G1 and flow out of a gas-closeable outlet O1. The electrode N may be a point, line, plane, or curved-shape electrode. A needle electrode is an example of a point electrode, and a trim blade is an example of a line electrode. Indeed, there may be multiple needles or other electrodes of the same polarity in the first atmospheric chamber, an arrangement especially useful for chemical agent monitors. A corresponding increase in detection sensitivity is observed when multiple electrodes (N) are used. The counter-electrode E0 contains a hole through which gas and charged particles can pass. It is set to a potential (for example, ground potential) that allows a corona or glow electrical discharge to be established between the electrode N and counter-electrode E0. The electrode may be either a cathode establishing a negative potential or an anode establishing a positive potential. In the electrical discharge, positive ions, electrons, and metastable excited-state atoms are formed. An additional electrode E1 is optionally placed at the exit of an optional second chamber C2 with closeable gas inlet G2 and closeable gas outlet O2. Electrode E1 also defines the entrance to third chamber C3 where an optional final electrode E2 is positioned at the exit.

In one current implementation, carrier gas is introduced from a gas cylinder into chamber C1 at a positive pressure. This causes flow of metastable excited-state atoms into chambers C2 and C3. In this implementation, the chambers have a volume of about one cubic centimeter. The orifices between chambers are about 3 mm in diameter and the flow through the orifices is on the order of a few milliliters per minute.

The carrier gases that have been used by the Applicants are helium and nitrogen. P-10 gas (90% argon+10% methane) and He/Ne mixtures are potential carrier gases. Also under consideration are argon and krypton. Indeed, any gas or mixture of gases with a metastable state lying higher than a state of the analyte is a potential carrier gas.

The corona or glow electrical discharge occurs in chamber C1. Chamber C2 provides an optional buffer region between chambers C1 and C3, and provides an option for introducing a reactant gas, for example, a gas that if ionized by metastable atoms to produce ions and electrons. Reactant gases are those that favor distinctive ion peaks by ion-molecule reactions. Typically, a small amount of reactant gas, such as ammonia (to promote ammonium ion attachment for positive ions), or a gas that produces chloride ions (e.g., methylene chloride, chloroform, or carbon tetrachloride for negative ions), can be used. Chloride ion addition has been shown to drastically enhance the detection of polynitro explosives by several orders of magnitude. The analyte may be introduced into chamber C3 and ions of analyte are extracted through a port in electrode E2 into the mass spectrometer atmospheric pressure interface or into the ion mobility spectrometer drift region. The device, or any part of it, can be heated to facilitate the analysis of compounds with low vapor pressures and to reduce sample carryover. While most preferred, the methods of the present invention do not require all three chambers.

Figure 2:
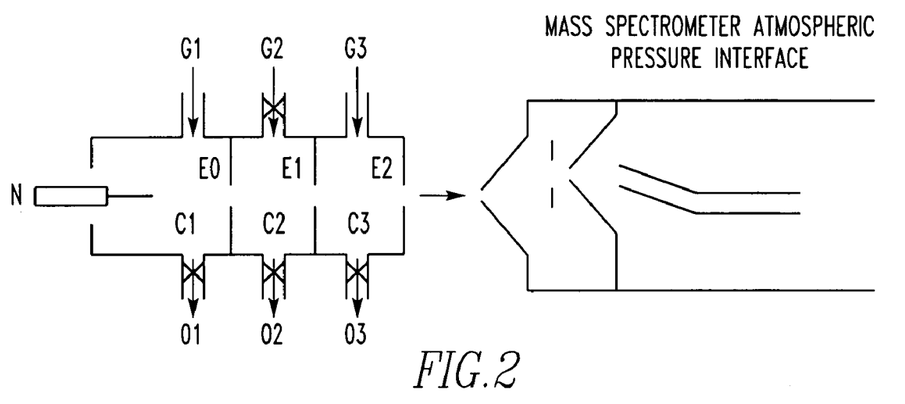
FIG. 2 is a schematic diagram of the atmospheric pressure ion source associated with a mass spectrometer.
Figure 3:
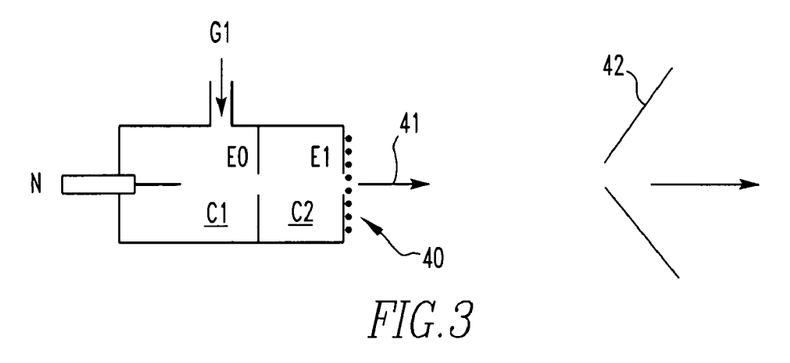
FIG. 3 is a schematic diagram of a simplified atmospheric pressure ion source having only two chambers.

FIG. 2 shows a specific configuration of the atmospheric ionization source for comparative operation where a carrier gas (for example, nitrogen or helium) flows into first chamber C1, passes through intermediate chamber C2, and exits final chamber C3 through a port in electrode E2. The ions and metastable gas molecules flow along the axis from needle electrode N through the ports in electrodes E0, E1, and E2. The device shown schematically in FIG. 2 was placed at the entrance cone ("orifice") of the atmospheric pressure interface of the JEOL AccuTOF® time-of-flight mass spectrometer.

The carrier gases with which Applicants have practiced the invention are helium and nitrogen. Both have high first electron ionization potentials and are not reactive with other elements or compounds at room temperature and pressure.

The discharge according to the present invention is either a corona discharge or a glow discharge. It is understood that in electrical discharges, electrons are accelerated into the atoms and molecules of the carrier gas causing additional electrons to be freed and accelerated in a cascading fashion. Collisions in addition to freeing electrons and creating positive ions transfer energy to atoms and molecules to create metastable excited-state species. A glow discharge is a luminous electrical discharge without sparks through a gas. A corona is a faint glow adjacent to the surface of an electrical conductor at high voltage. Typically, glow discharges require a large potential to initiate but a lower voltage to be sustained following "breakdown". The internal resistance of the power supply for the needle electrode and other factors limit the current in the discharge. Higher currents that might result in sputtering or arcing would not be according to the present invention.

The atmospheric pressure ionization method described herein is useful for the introduction of ions into mass spectrometers and ion mobility spectrometers for the detection and identification of analytes of interest, such as drugs, explosives, chemical weapons, toxic industrial materials, and the like. It is non-radioactive and provides rapid sampling of gas and vapor in headspace sampling. It also permits rapid and direct sampling of chemicals on surfaces.

Figure 4:
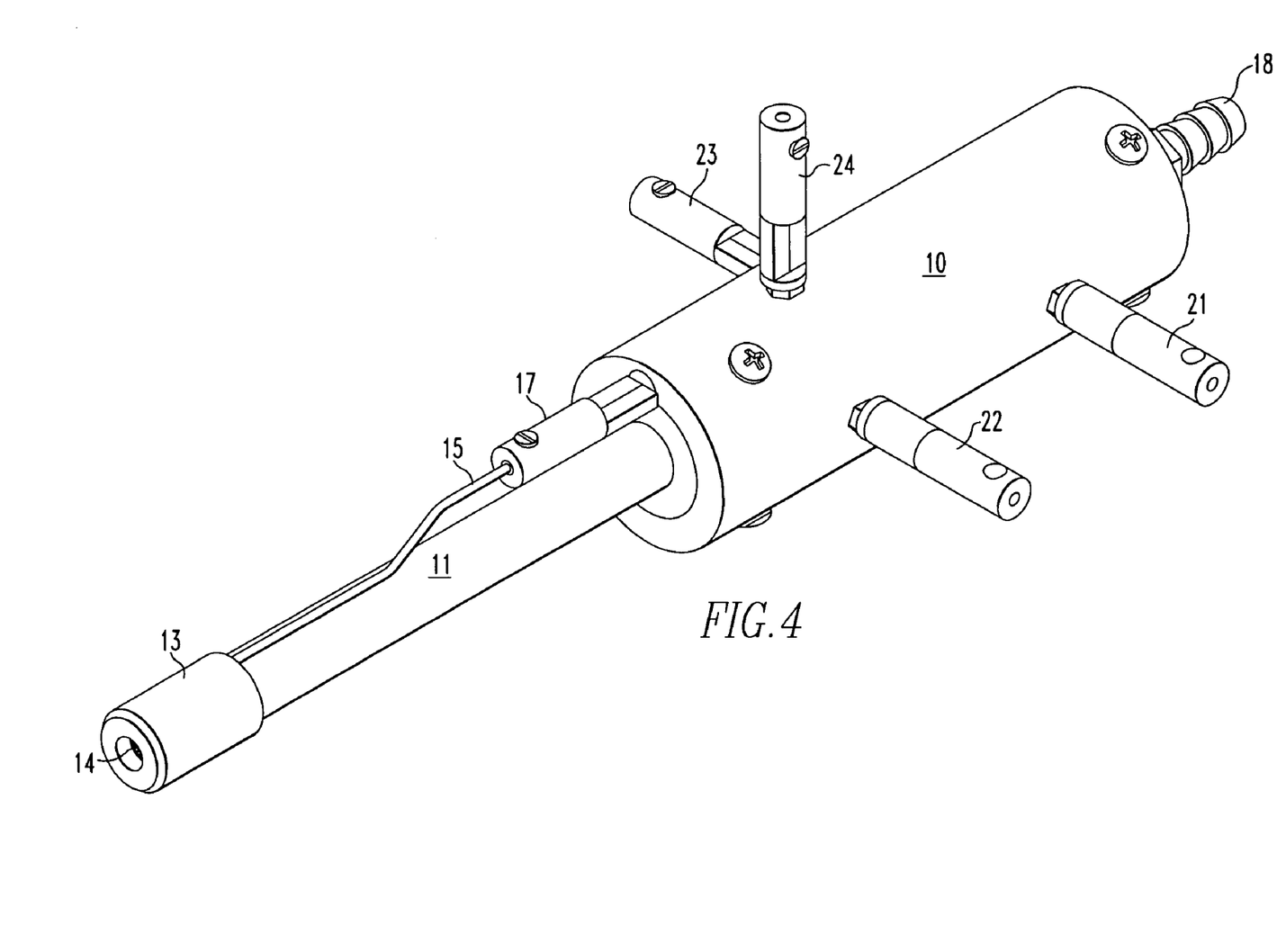
FIG. 4 is a perspective view of an atmospheric pressure interface or device useful according to the present invention at scale 2:1.

Referring now to FIG. 4, a physical implementation of an atmospheric pressure ion device useful according to the present invention may comprise a tubular non-conductive casing 10 which may be fabricated from a Teflon®-type plastic (good temperature resistance), a ceramic material, or other non-conductive material. Extending from one end of the casing is a disposable glass tube insert 11 with a non-conductive end piece 13 that serves to hold a mesh electrode or grid 14 in place. The mesh electrode 14 is connected by an insulated wire 15 to a micro-jack 17 on the casing. At the opposite end of the casing 10 is a carrier gas inlet comprising a connector 18 with a corrugated surface for holding a flexible tube slide thereon. Micro-jacks 21, 22, 23, and 24 are threaded in the casing for connecting leads from a power supply to the various electrodes within the casing 10.

Figures 5, 6:
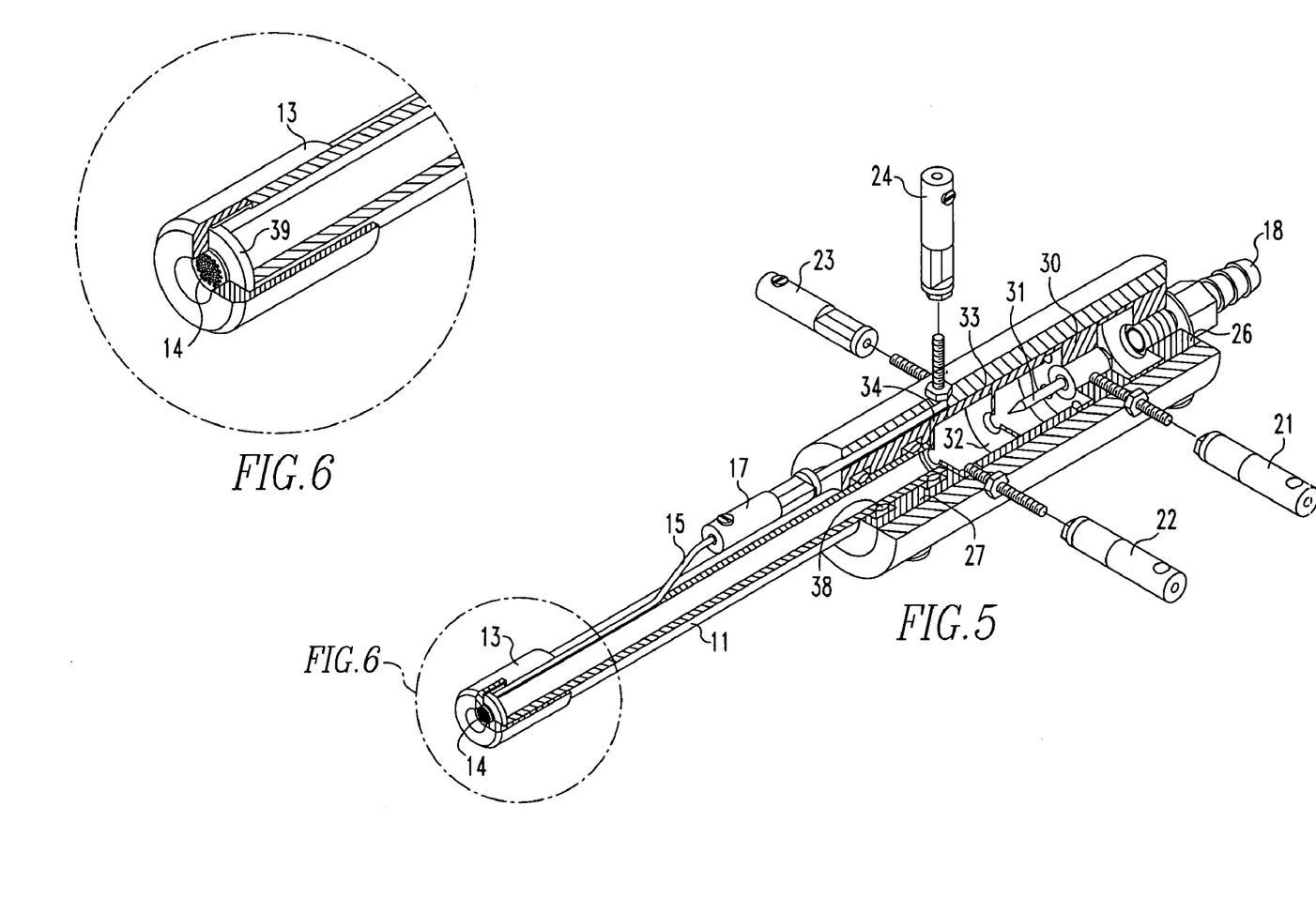
FIG. 5 is a broken away perspective view similar to FIG. 4.
FIG. 6 is a detail from the perspective view of FIG. 5.

Referring now to FIG. 5, the interior of the casing is divided into first and second chambers. At each axial end, a hollow plug is fixed to the casing. At the inlet end, a plug 26 has threads for receiving the inlet connector 18. At the outlet end, a plug 27 is provided with interior annular grooves for receiving Viton O-rings 38 that seal against the exterior surface of the glass tube insert 11. Non-conductive spacer 30 holds the needle electrode 31 which is connected to micro-jack 21 and defines a first chamber in which a corona or glow electrical discharge is created. A conductive spacer and electrode baffle 32 are positioned within the casing and adjacent to the non-conductive spacer supporting the needle. The conductive spacer 32 is connected to micro-jack 23. A non-conductive spacer 33 is positioned within the casing and is adjacent to the conductive spacer 32 to define a second chamber. Another conductive spacer and electrode baffle 34 are positioned adjacent to the non-conductive spacer 33 to define the axial outlet end of the second chamber. The conductive spacer 34 abuts the glass tube insert 11. This conductive spacer is connected to micro-jack 22. The micro-jack 24 is in communication with an electrical conduit that runs axially to the outlet end of the casing where it connects to a micro-jack 17.

Referring to FIG. 6, the end of the glass tube with the non-conductive end piece 13 is shown in more detail. The nonconductive end piece 13 spaces the grid from direct contact making it difficult to come into contact with the high voltage on the grid. The hole in the end piece allows the escape of the excited-state gas to ionize the analyte. A copper washer 39 (see FIG. 7) abuts the end of the glass tube and is soldered to lead 15. Held against the washer is a grid electrode 14. The hollow glass tube 11 and grid electrode 14 define a third chamber.

Figure 7:
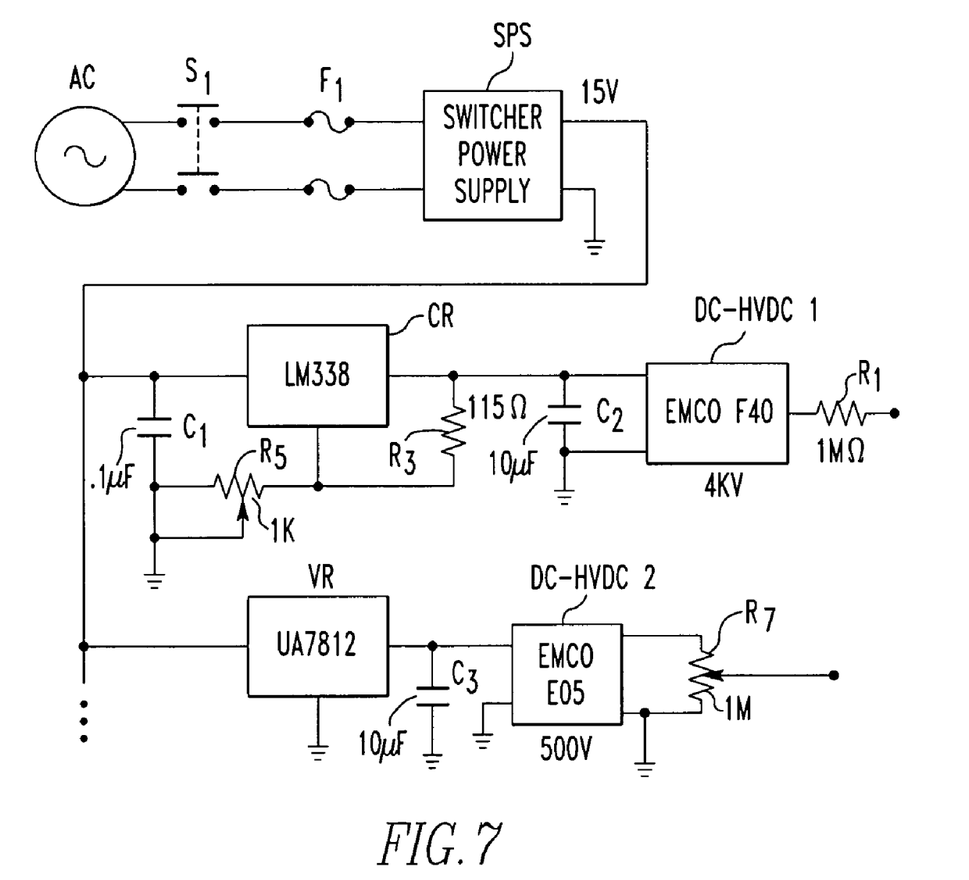
FIG. 7 is a schematic circuit diagram of a power supply for an atmospheric pressure device or source useful according to the present invention.

Referring to FIG. 7, an example of a power supply for an atmospheric pressure ion source is shown schematically. AC current passes switch $S_1$ and fuse $F_1$ and is applied to switcher power supply SPS. The 15 volt DC output is applied across filter capacitor $C_1$ to current regulator CR. The regulated current is applied across filter capacitor $C_2$ to the high voltage direct current converter DC-HVDC. The high voltage of this device is applied through current limit resistor $R_1$ to the electrode for creating a corona or glow discharge. The 15 volt output is also applied to a plurality of general purpose high current positive voltage regulators VR. The output of the voltage regulators is applied across filter capacitor $C_3$ to pass current to high voltage direct converters $DC-HVDC_2$. The output of the converters is applied to potentiometers $R_7$ enabling adjustment of the potential on the lens electrodes. Those skilled in power supply design will understand how to configure a circuit for negative output potentials.

The atmospheric pressure ionization method described herein is useful for the introduction of ions into mass spectrometers and ion mobility spectrometers for the detection and identification of analytes of interest, such as drugs, explosives, chemical weapons, toxic industrial materials, and the like. It is non-radioactive and provides rapid sampling of gas and vapor in headspace sampling. It also permits rapid and direct sampling of chemicals on surfaces. This feature makes the ion source described herein a very useful replacement for a radioactive source on IMS detectors.

EXAMPLE 1

Figure 8A:
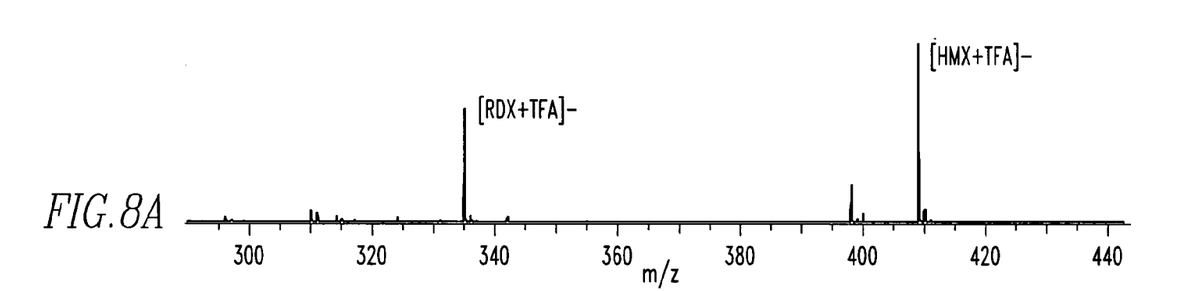
FIGS. 8A, 8B, and 8C comprise mass spectra produced by the method of the present invention, wherein the reactant gas is trifluoroacetate.
Figure 8B:
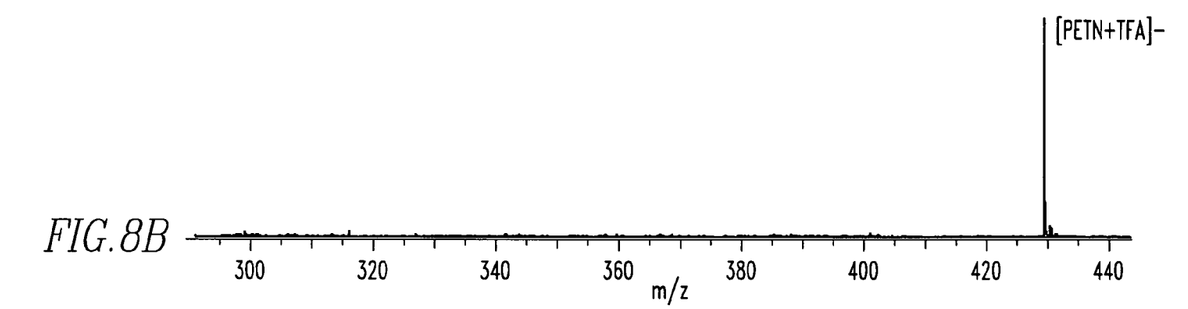
Figure 8C:
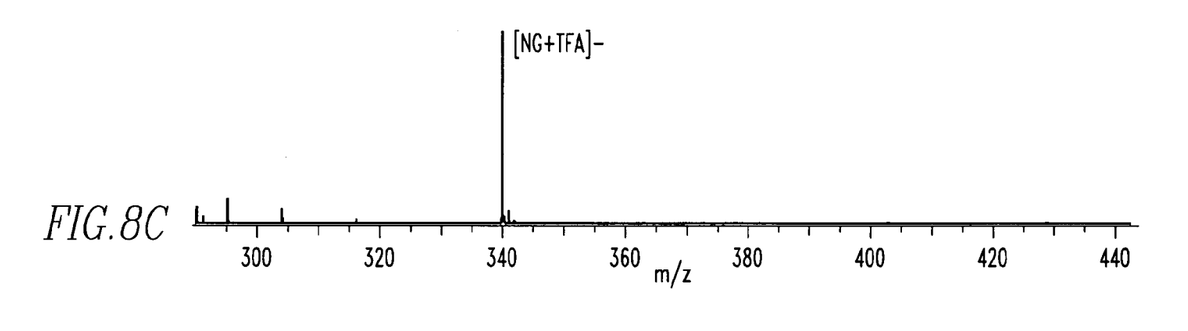

In this example, helium was passed through a first chamber at atmospheric pressure in which an electrical discharge was maintained. The helium was passed out of the first chamber into a second camber or headspace-containing vapor from a solution of 0.1 trifluoroacetic acid to form trifluoroacetate (TFA) ions. The gas mixture containing TFA ions (mol. wt. 113) were directed at surfaces contaminated with explosives HMX (mol. wt. 296), RDX (mol. wt. 222.15), PETN (mole. wt. 316) and NG (mol. wt. 227). The gas directed off the surfaces was allowed to enter the mass spectrometer and the following adduct peaks were identified as shown in FIGS. 8A, 8B, and 8C:

1. RDX+TFA (mol. wt. 335)
2. HMX+TFA (mol. wt. 409)
3. PETN+TFA (mol. wt. 429)
4. NG+TFA (mol. wt. 340)

Substantially identical results have been obtained holding a vial containing 0.5% TFA in acetonitrile below the contaminated surfaces.

Other suitable halogen-containing compounds, such as methylene chloride, carbon tetrachloride, or chloroform, may be used to form chlorine ion species or chlorine cluster ions that react to produced adduct species $[M+Cl]^-$. As an example, this is useful for identifying explosives such as nitroglycerin, tetryl, RDX or HMX, that do not produce molecular anions. The Applicants have found that other anions, such as acetate $(CH_3CO_2)^-$ ions, can be used for the same purpose to form adjunct ions of these explosives.

EXAMPLE 2

Figure 9:
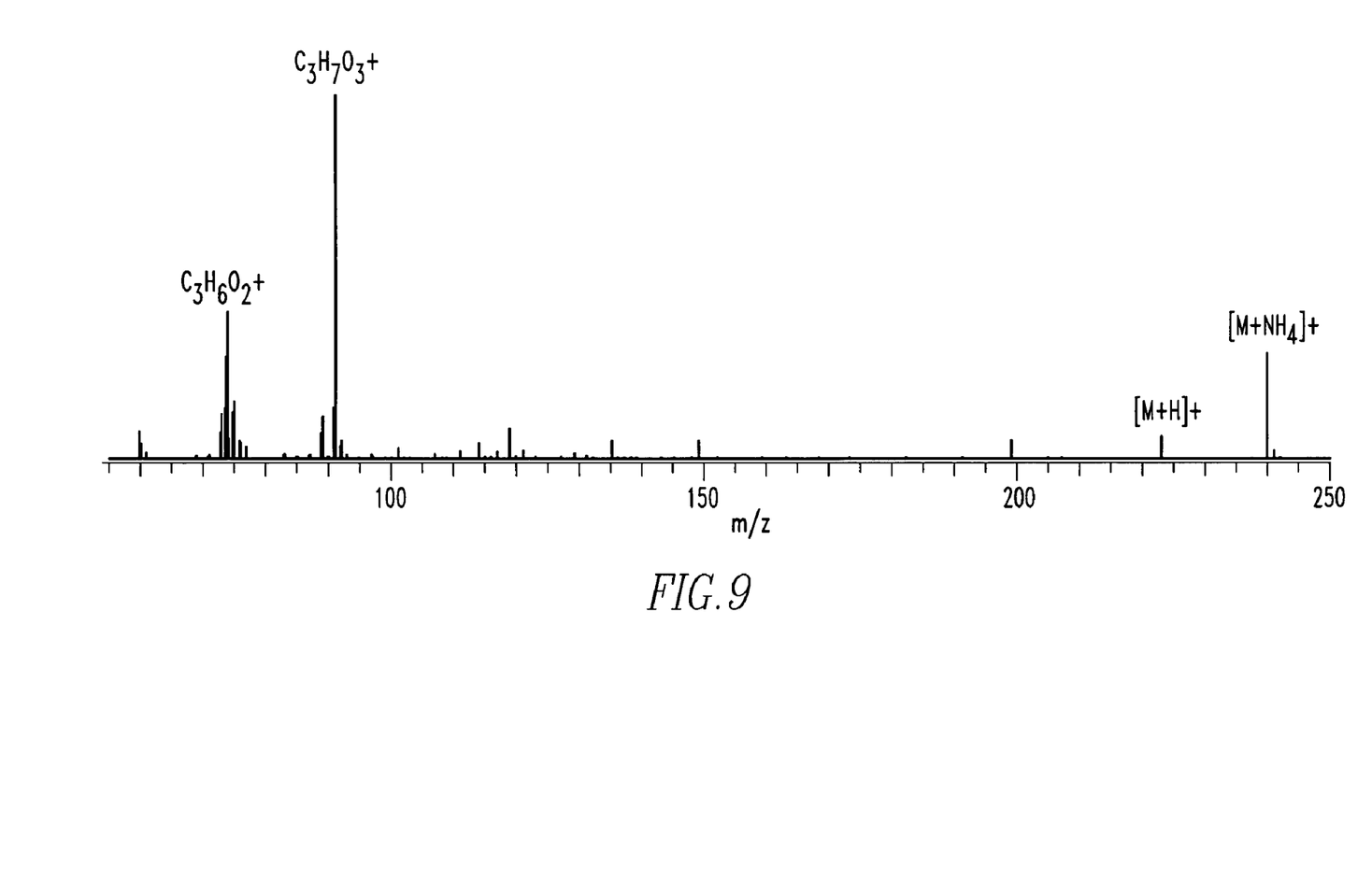
FIG. 9 comprises a mass spectrum produced by the method of the present invention, wherein the reactant gas is ammonia.

In this example, the reactant gas was the vapor from a solution of $NH_4OH$ in water. The helium and reactant gas mixture was directed against a surface contaminated with TATP, a common terrorist explosive (mol. wt. 222). A strong peak in the mass spectrum (see FIG. 9) is found at 238 (TATP+$NH_4$).

EXAMPLE 3

Figure 10A:
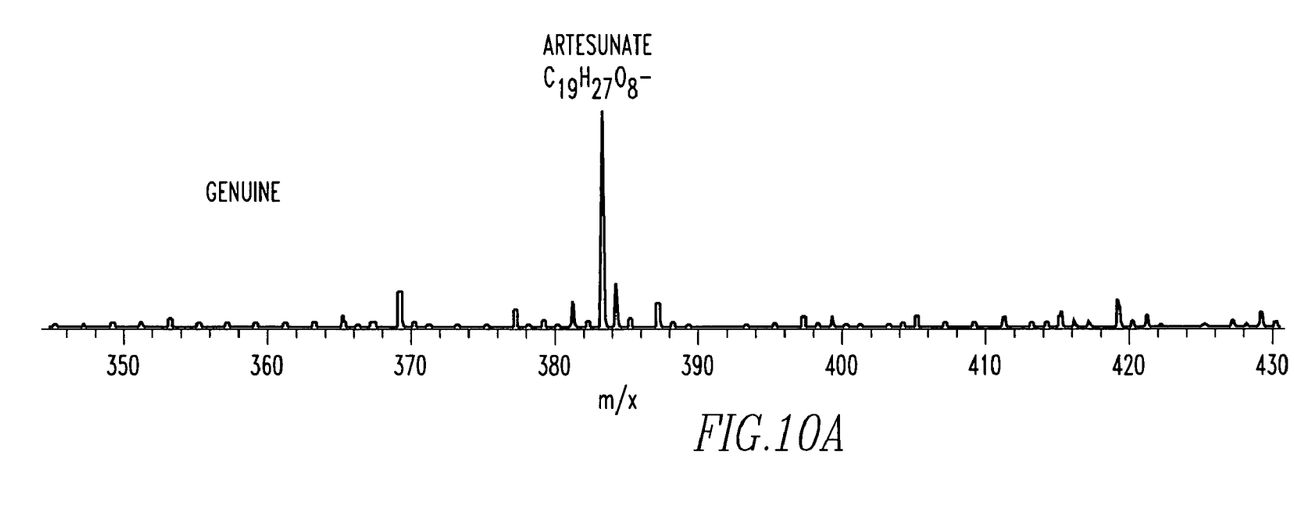
FIGS. 10A and 10B comprise mass spectra produced by the method of the present invention, wherein the reactant gas is water vapor.
Figure 10B:
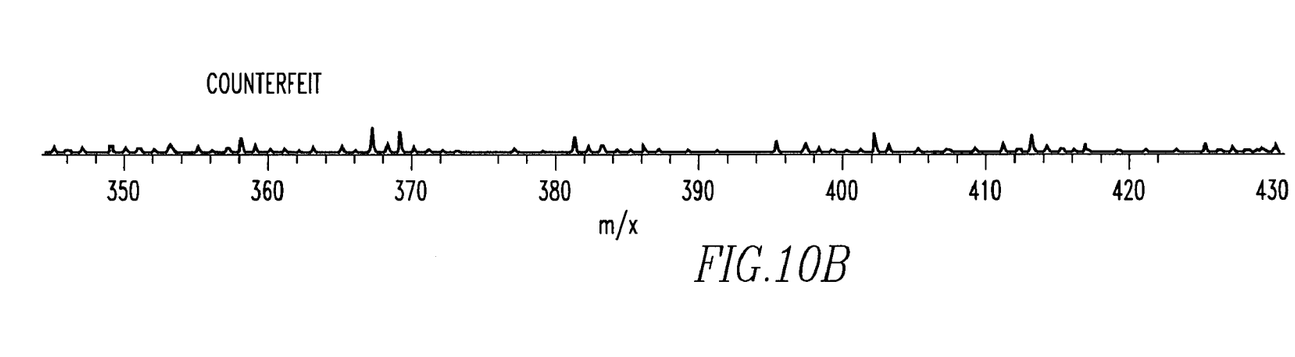

In this example, the reactant gas was water vapor. The drug artesunate taken in tablet form as a treatment for malaria is legitimately prepared by Guilin Pharma. It is massively counterfeited in South East Asia. With no sample preparation, the real and counterfeited drugs can be distinguished by the method disclosed herein. The active ingredient artesunate has a molecular weight of 283. The mass spectra of real and counterfeit drugs are shown in FIGS. 10A and 10B. The tablets were simply placed near the entrance to the mass spectrometer and the He/water vapor reactant gas was blown at the tablets.

As used herein, an "atmospheric ionization source" is one that does not require a vacuum pump. Of course, the analyzer (mass spectrometer) may require vacuum pumps, but the ions are formed at pressures somewhat above and below atmospheric pressure.

EXAMPLE 4

Figure 11A:
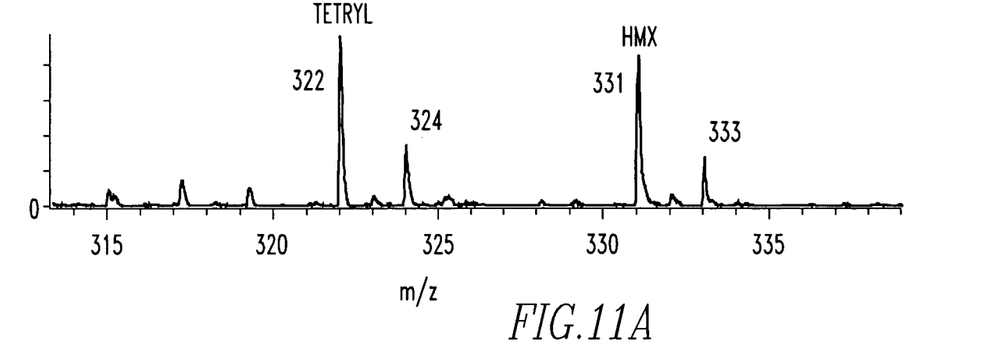
FIGS. 11A and 11B comprise mass spectra produced by the method of the present invention wherein the reactant gas is trichloromethane.
Figure 11B:
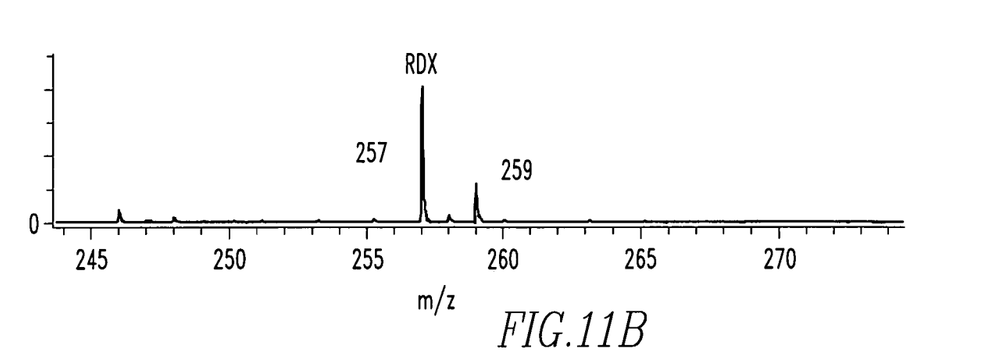

In this example, the reactant gas (dopant) was trichloromethane. The helium and reactant gas mixture was directed against a surface contaminated with the explosives Tetryl, HMX, and RDX. The $[M+Cl]^-$ ions were easily detected as shown by the strong peaks for each in the mass spectra illustrated in FIGS. 11A and 11B.

Having thus described our invention in the detail and particularity required by the Patent Laws, what is desired protected by Letters Patent is set forth in the following claims.

The invention claimed is:

1. A method of producing analyte, analyte fragment, and/or analyte adduct ions for mass spectrographic analysis comprising the steps of:
   introducing a carrier gas at atmospheric pressure into a first chamber;
   establishing a potential difference in the chamber creating metastable neutral excited-state species;
   directing the carrier gas and metastable species from the chamber into a reactant gas at atmospheric pressure wherein the metastable species interact with the reactant gas to produce ionized derivatives of the reactant gas; and
   directing the carrier-gas/reaction-gas/ionized-derivative mixture into contact with the analyte maintained at atmospheric pressure and near ground potential to form analyte ions, analyte fragment ions, and/or analyte adduct ions.

2. The method of claim 1, wherein the carrier gas consists substantially entirely of one or more of nitrogen and noble gases with an available metastable state high enough to cause ionization of the reactant gas.

3. The method of claim 2, wherein the chamber comprises an electrode and a counter-electrode having a potential therebetween sufficient to cause an electrical discharge in the carrier gas.

4. The method of claim 2, wherein the chamber comprises and electrode and a counter-electrode across which a high frequency signal is applied to cause an electrical discharge in the carrier gas.

5. The method of claim 2, wherein the chamber comprises an electrode and counter-electrode each separated by a dielectric barrier from the carrier gas having a potential therebetween sufficient to cause an electrical discharge in the carrier gas.

6. The method of claim 2, wherein the reactant gas is introduced into a second atmospheric pressure chamber in communication with the first atmospheric pressure chamber and the ionized derivatives of the reactant gas are formed therein.

7. The method of claim 2, wherein the reactant gas is added in trace amounts in the atmosphere near the analyte.

8. The method of claim 2, wherein the reactant gas comprises water vapor and the ionized derivatives comprise positive ion (protonated) water molecules and water molecule clusters.

9. The method of claim 2, wherein the reactant gas comprises oxygen and the ionized derivatives comprise negative oxygen ions and/or negative oxygen ion water clusters.

10. The method of claim 2, wherein the reactant gas comprises ammonia and the ionized derivatives comprise positive ion ammonia and ammonia water ion clusters.

11. The method of claim 2, wherein the reactant gas comprises a volatile organic molecule.

12. The method of claim 11, wherein the reactant gas comprises a halogen-containing molecule.

13. The method of claim 11, wherein the volatile organic molecule is trifluoroacetate.

14. The method of claim 2, wherein the analyte is non-volatile.

15. The method of claim 2, wherein the analyte is ionized at a liquid or solid surface.

16. The method of claim 1, wherein the potential difference is established by electrodes one of which is a needle electrode.

* * * * *

UNITED STATES PATENT AND TRADEMARK OFFICE
CERTIFICATE OF CORRECTION

| | | |
|---|---|---|
| PATENT NO. | : 7,112,785 B2 | Page 1 of 1 |
| APPLICATION NO. | : 11/034450 | |
| DATED | : September 26, 2006 | |
| INVENTOR(S) | : Laramee et al. | |

It is certified that error appears in the above-identified patent and that said Letters Patent is hereby corrected as shown below:

<u>Title Page</u>, See Item (56) References Cited, OTHER PUBLICATIONS, the second reference, "Kjichiro Otsuka et al." should read -- Kiichiro Otsuka et al. --

<u>Column 10</u>, Lines 36-37, Claim 4, "comprises and electrode" should read -- comprises an electrode --

Signed and Sealed this

Sixth Day of February, 2007

JON W. DUDAS
*Director of the United States Patent and Trademark Office*